(12) United States Patent
    Steel et al.

(10) Patent No.: US 10,806,864 B2
(45) Date of Patent: Oct. 20, 2020

(54) ELECTRONIC MODULE AND DRUG DELIVERY DEVICE

(71) Applicant: Sanofi-Aventis Deutschland GMBH, Frankfurt am Main (DE)

(72) Inventors: Samuel Steel, Warwickshire (GB); Paul Richard Draper, Worcestershire (GB); Joseph Butler, Warwickshire (GB); George Cave, Warwickshire (GB); David Richard Mercer, Dorset (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 16/148,854

(22) Filed: Oct. 1, 2018

(65) Prior Publication Data
    US 2019/0030250 A1    Jan. 31, 2019

Related U.S. Application Data

(63) Continuation of application No. 14/762,488, filed as application No. PCT/EP2014/051475 on Jan. 27, 2014, now Pat. No. 10,086,141.

(30) Foreign Application Priority Data

Jan. 29, 2013  (EP) .................................... 13153141

(51) Int. Cl.
    *A61M 5/31*     (2006.01)
    *A61M 5/20*     (2006.01)
    (Continued)

(52) U.S. Cl.
    CPC ................ *A61M 5/31* (2013.01); *A61M 5/20* (2013.01); *G06F 1/16* (2013.01); *H01R 24/66* (2013.01);
    (Continued)

(58) Field of Classification Search
    CPC ........ H01R 27/00; H01R 31/06; H01R 13/64; H01R 13/642; H01R 13/6456;
    (Continued)

(56) References Cited

U.S. PATENT DOCUMENTS 5,679,017 A    10/1997  Smith
6,932,654 B2    8/2005  Washino
(Continued)

FOREIGN PATENT DOCUMENTS

JP    2011-517581    6/2011
JP       3176945     7/2012
(Continued)

OTHER PUBLICATIONS

Examination, Communication pursuant to Article 94(3) EPC issued in European Patent Application No. 14 701 392.4, dated Apr. 10, 2018.
(Continued)

*Primary Examiner* — Gary F Paumen
(74) *Attorney, Agent, or Firm* — Fish & Richardson P.C.

(57) ABSTRACT

The invention relates to an electronic module for recording information of a drug delivery device, the electronic module comprising at least one connector, wherein at least one connector is adapted to be connected to a port of the drug delivery device and wherein at least one connector is adapted to be connected to a port of a computer. Furthermore, the invention relates to a drug delivery device, comprising a port for connecting to the connector of the electronic module.

17 Claims, 13 Drawing Sheets

(51) Int. Cl.
*G06F 1/16* (2006.01)
*H01R 24/66* (2011.01)
*H01R 27/00* (2006.01)
*A61M 5/142* (2006.01)
*H01R 13/64* (2006.01)
*H01R 24/62* (2011.01)
*H01R 103/00* (2006.01)

(52) U.S. Cl.
CPC ......... *H01R 27/00* (2013.01); *A61M 5/14244* (2013.01); *A61M 2005/3125* (2013.01); *A61M 2205/33* (2013.01); *A61M 2205/52* (2013.01); *A61M 2205/8206* (2013.01); *A61M 2205/8262* (2013.01); *H01R 13/64* (2013.01); *H01R 24/62* (2013.01); *H01R 2103/00* (2013.01); *H01R 2201/12* (2013.01)

(58) Field of Classification Search
CPC ............... H01R 13/631; H01R 13/629; H01R 23/7005; H01R 24/62; H01R 24/66; H01R 2201/12; H01R 2103/00; G06F 1/16; A61M 5/312; A61M 5/14244; A61M 2205/8262; A61M 2205/52; A61M 2205/8206; A61M 2205/33; A61M 2005/3125
USPC ............... 439/172, 171, 218, 680, 377, 374
See application file for complete search history.

(56) References Cited

U.S. PATENT DOCUMENTS

| | | | |
|---|---|---|---|
| 7,021,971 B2 | 4/2006 | Chou et al. | |
| 7,094,086 B2 | 8/2006 | Teicher | |
| 7,121,850 B2 | 10/2006 | Yeh | |
| 7,517,253 B1 | 4/2009 | Chiang | |
| 7,537,471 B2 | 5/2009 | Teicher | |
| 7,727,027 B2 | 6/2010 | Chiang et al. | |
| 8,198,563 B2 | 6/2012 | Tsai | |
| 8,292,654 B2* | 10/2012 | Yasui | H01R 12/724 439/378 |
| 8,408,940 B2 | 4/2013 | Chang | |
| 8,480,436 B2* | 7/2013 | Chang | H01R 12/724 439/660 |
| 8,485,851 B2 | 7/2013 | Kondo et al. | |
| 8,715,010 B2* | 5/2014 | Wang | H01R 13/7031 439/660 |
| 8,734,172 B2* | 5/2014 | Takei | H01R 12/7005 439/248 |
| 8,784,123 B1 | 7/2014 | Leiba et al. | |
| 8,888,744 B2 | 11/2014 | Yodfat et al. | |
| 9,004,951 B2* | 4/2015 | Wu | H01R 27/00 439/638 |
| 10,086,141 B2* | 10/2018 | Steel | H01R 24/66 |
| 2003/0013336 A1 | 1/2003 | Kuroda | |
| 2006/0099840 A1 | 5/2006 | Yeh | |
| 2007/0178735 A1 | 8/2007 | Chen | |
| 2009/0311895 A1 | 12/2009 | Chen | |
| 2010/0015831 A1 | 1/2010 | Miyoshi | |
| 2011/0009824 A1 | 1/2011 | Yodfat et al. | |
| 2011/0098241 A1 | 4/2011 | Sun et al. | |
| 2011/0130019 A1 | 6/2011 | Lim et al. | |
| 2012/0252245 A1 | 10/2012 | Chang | |
| 2013/0164993 A1 | 6/2013 | Wang et al. | |
| 2015/0180147 A1 | 6/2015 | Sun et al. | |
| 2015/0288115 A1 | 10/2015 | Tsai | |
| 2016/0081543 A1 | 3/2016 | Mowrey et al. | |

FOREIGN PATENT DOCUMENTS

| | | |
|---|---|---|
| JP | 3178072 | 8/2012 |
| JP | 2013-532351 | 8/2013 |
| TW | M414006 | 10/2011 |
| WO | WO 2008/065256 | 6/2008 |
| WO | WO 2009/062675 | 5/2009 |
| WO | WO 2009/113060 | 9/2009 |
| WO | WO 2011/117404 | 9/2011 |
| WO | WO 2011/150403 | 12/2011 |
| WO | WO 2013/117724 | 8/2013 |

OTHER PUBLICATIONS

English Translation of First Office Action issued in Chinese Patent Application 201480005950.1, dated May 2, 2017.
English Translation of Notice of Reason(s) for Rejection issued in Japanese Patent Application No. 2015-554171, dated Oct. 25, 2017.
XP-002699523, Apple USB Extension Cable, http://wayback.archive.org/web/*/http:/fmezzanin.tistory.eom/609, Dated Jun. 26, 2013.
International Search Report in Application No. PCT/EP2014/051475, dated Feb. 27, 2014, 3 pages.
International Preliminary Report on Patentability and Written Opinion in Application No. PCT/EP2014/051475, dated Aug. 4, 2015, 6 pages.

\* cited by examiner

ELECTRONIC MODULE AND DRUG DELIVERY DEVICE

CROSS REFERENCE TO RELATED APPLICATIONS

The present application is a continuation of U.S. patent application Ser. No. 14/762,488, filed Jul. 22, 2015, which is a U.S. National Phase Application pursuant to 35 U.S.C. § 371 of International Application No. PCT/EP2014/051475 filed Jan. 27, 2014, which claims priority to European Patent Application No. 13153141.0 filed Jan. 29, 2013. The entire disclosure contents of these applications are herewith incorporated by reference into the present application.

FIELD OF INVENTION

The invention relates to an electronic module for recording information of a drug delivery device and to a drug delivery device arranged to connect to the electronic module.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Drug delivery devices may be arranged to allow recording information related to the therapy such as type and volume of a drug and injection time and date.

WO 2009/113060 A2 discloses a portable ambulatory fluid delivery device. The device includes a dispensing unit to dispense therapeutic fluid, the dispensing unit including one or more rechargeable batteries, a housing to retain the one or more rechargeable batteries, a reservoir to contain the therapeutic fluid, a driving mechanism to cause delivery of the therapeutic fluid from the reservoir to a user's body, and at least one electrical connector to be coupled to a recharging unit to direct electrical power received from the recharging unit to recharge the one or more rechargeable batteries. At least a portion of the housing is securable to a skin of the user.

SUMMARY

It is an object of the present invention to provide an improved electronic module for recording information of a drug delivery device and to provide an improved drug delivery device.

The object is achieved by an electronic module according to claim 1 and by a drug delivery device according to claim 12.

Preferred embodiments of the invention are given in the dependent claims.

According to the invention an electronic module for recording information of a drug delivery device comprises at least one connector, wherein at least one connector is adapted to be connected to a port of the drug delivery device and wherein at least one connector is adapted to be connected to a port of a computer distinct from the port of the drug delivery device, i.e. the port of the computer and the port of the drug delivery device are distinctly shaped.

A computer in the context of this application may be any data processing device suitable for reading and processing data recorded on the electronic module, such as a personal computer, laptop, handheld, tablet computer or smart phone.

The at least one connector is adapted to be directly connected to the port of the drug delivery device and/or to a port of a blood glucose meter. The blood glucose meter may likewise be integrated with the drug delivery device. Furthermore, the same or another one of the at least one connectors is adapted to interface with the computer via a universal connection. The drug delivery device and/or the electronic module are/is adapted to record therapy information, such as quantities of drug dialled and/or dispensed, dispense time and date etc., to aid health care professionals' understanding of a patient's medicinal requirements. In connection with the blood glucose meter the electronic module may be adapted to record blood glucose values and, if applicable, time and date of performed blood glucose measurements.

The electronic module may comprise a display for displaying information to a user. The electronic module may be arranged to collect and display to the user information such as:

type of drug in the current cartridge 4 (long acting insulin, short acting insulin, GLP-1, etc.),
drug volume remaining in the cartridge 4,
use-by date of the drug in the current cartridge 4,
sizes and timings of doses of the drug taken,
time of next recommended blood glucose test, and
number of blood glucose measurement strips remaining.

The drug delivery device and/or blood glucose meter may comprise sensors for acquiring this information.

The electronic module aims to reduce the complexity of diabetes care and provide a complete therapy history for both health care professionals and patients. The electronic module may be arranged to run on-board software for displaying the data collected in a clear manner, highlighting trends in the patient's medication. The electronic module is arranged as a re-useable device. The electronic module may have stored software allowing it to interface with a computer without losing functionality.

The re-useable electronic module also allows the compatible drug delivery device to be disposable; as a significant amount of complexity can be removed from the drug delivery device with a limited number of metallic components.

The connector of the electronic module may be arranged as a universal or standard connector, for example in one of the formats USB, USB-B, Mini USB, Micro USB, IEEE1394, computer serial port (RS232), SD Card, Mini SD Card, Micro SD Card, MultiMediaCard, CompactFlash, Memory Stick, etc.

In an exemplary embodiment the electronic module may comprise one connector both adapted to be connected to the port of the drug delivery device and adapted to be connected to the port of the computer.

In another exemplary embodiment the electronic module may comprise two connectors, wherein a first one of the connectors is adapted to be connected to the port of the drug delivery device and wherein a second one of the connectors is adapted to be connected to the port of the computer. The first connector may be a customized connector while the second connector may be a universal connector.

In an exemplary embodiment the connector may comprise at least one slot or recess adapted to be engaged by a protrusion arranged on the port of the drug delivery device. The connector may correspond to a universal connector except for the slot or recess thus allowing the connector to connect to both a universal port without a protrusion and to a customized port having the protrusion. The protrusion in the customized port however does not allow connection of a universal connector thus preventing the user from connecting universal devices, for example a USB memory stick.

In an exemplary embodiment the connector comprises a contact carrier retaining a plurality of electric contacts arranged within a frame, wherein a portion of a space within the frame is empty and dimensioned to allow insertion of a contact carrier of the correspondingly shaped port of the drug delivery device retaining a plurality of electric contacts for contacting the electric contacts of the connector.

In an exemplary embodiment the slot may be formed in the frame.

In another exemplary embodiment the recess is arranged in the electronic module or in the connector behind the contact carrier, e.g. in an otherwise compact part of the connector or electronic module such as a housing.

In an exemplary embodiment of the plurality of electric contacts is located so as to allow contacting each electric contact of the port of the computer by at least two electric contacts of the connector of the electronic module and to allow contacting each electric contact of the port of the drug delivery device by one respective electric contact of the connector of the electronic module. Thus, the amount of information transmittable between the electronic module and the drug delivery device is increased without having to provide complex circuitry in the drug delivery device while still allowing the electronic module to contact a universal port.

For example, as opposed to a universal connector the contacts in the customized connector may be split transversally or longitudinally once or more thus obtaining a multiple of the number of contacts of the universal connector. The port of the drug delivery device would also be modified to have its electric contacts split transversally or longitudinally for obtaining a corresponding number of electric contacts.

In an exemplary embodiment the plurality of electric contacts is located so as to allow contacting the electric contacts of the port of the computer by a first one of two subsets of the electric contacts of the connector of the electronic module and to allow contacting each electric contact of the two subsets by one respective electric contact of the port of the drug delivery device. Thus, the amount of information transmittable between the electronic module and the drug delivery device is increased without having to provide complex circuitry in the drug delivery device while still allowing the electronic module to contact a universal port.

In an exemplary embodiment the electric contacts of the first subset are narrower than the electric contacts of the port of the computer, wherein each contact of a second one of the two subsets is arranged between two contacts of the first subset. The electric contacts of the second subset are preferably arranged such that they do not contact the electric contacts of the port of the computer but insulated areas between the electric contacts of the port of the computer.

In an exemplary embodiment the electric contacts of the first subset are arranged on a first plane of the contact carrier and the electric contacts of the second subset are arranged on at least one further plane of the contact carrier. The electric contacts of the first subset on the first plane are arranged to contact both, corresponding electric contacts in the ports of the computer and the drug delivery device while the electric contacts of the second subset on the further plane are arranged to contact corresponding electric contacts on a corresponding plane of the contact carrier in the port of the drug delivery device only. This corresponding plane of the port of the drug delivery device also distinguishes the port from a universal port and prevents connecting it to a universal connector.

According to another aspect of the invention a drug delivery device comprises a port for connecting to a connector of an electronic module according to the invention for recording information of a drug delivery device.

In an exemplary embodiment the port comprises at least one protrusion adapted to engage a slot or recess in the connector of the electronic module.

In an exemplary embodiment the port comprises a contact carrier retaining a plurality of electric contacts arranged within a frame, wherein a portion of a space within the frame is empty and dimensioned to allow insertion of a contact carrier of the correspondingly shaped connector of the electronic module retaining a plurality of electric contacts for contacting the electric contacts of the port.

In an exemplary embodiment a gap is provided between the contact carrier and the frame of the port to allow insertion of the frame of the connector.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
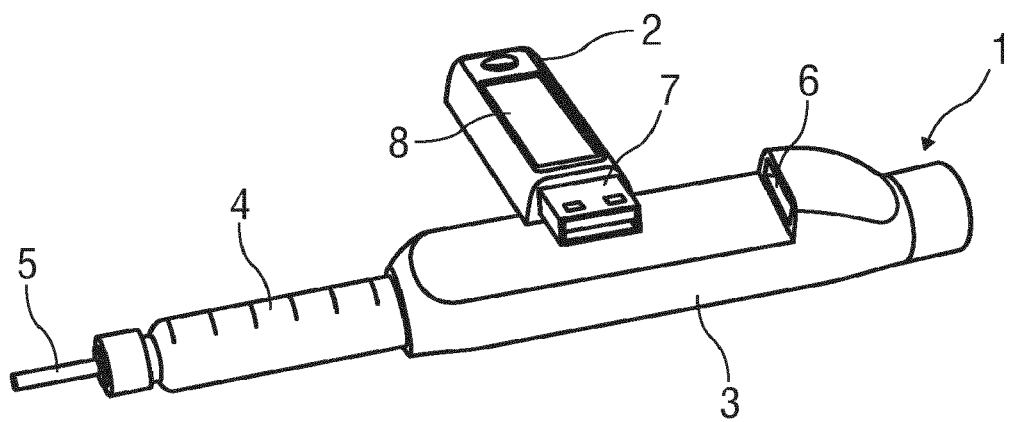
FIG. 1 is a schematic view of a drug delivery device and an electronic module.

FIG. 1 shows a drug delivery device 1 and an electronic module 2.

The drug delivery device 1 comprises a body 3 adapted to receive a drug cartridge 4 or syringe having or adapted to be connected to a hypodermic injection needle 5 or needle arrangement. Furthermore, the drug delivery device 1 comprises a port 6 for interfacing with the electronic module 2.

The electronic module 2 comprises a connector 7 adapted to be directly connected to the port 6 of the drug delivery device 1 and/or to a port of a blood glucose meter (not illustrated). The blood glucose meter may likewise be integrated with the drug delivery device 1. Furthermore, the electronic module 2 is adapted to interface with a computer, such as a PC or Laptop via a universal connection. The drug delivery device 1 and/or the electronic module 2 are/is adapted to record therapy information, such as quantities of drug dialled and/or dispensed, dispense time and date etc., to aid health care professionals' understanding of a patient's medicinal requirements. In connection with the blood glucose meter the electronic module 2 is adapted to record blood glucose values and, if applicable, time and date of performed blood glucose measurements.

The electronic module 2 is adapted to record the date and time of any treatment related activity, in addition to recording the blood glucose reading or the drug dose size taken.

The electronic module 2 comprises a display 8 for displaying information to a user. The electronic module 2 may be arranged to collect and display to the user information such as:

type of drug in the current cartridge 4 (long acting insulin, short acting insulin, GLP-1, etc.),
drug volume remaining in the cartridge 4,
use-by date of the drug in the current cartridge 4,
time of next recommended blood glucose test, and
number of blood glucose measurement strips remaining.

The drug delivery device 1 may comprise sensors for acquiring this information.

The electronic module 2 aims to reduce the complexity of diabetes care and provide a complete therapy history for both health care professionals and patients. The electronic module 2 may be arranged to run on-board software for displaying the data collected in a clear manner, highlighting trends in the patient's medication. The electronic module 2 is arranged as a re-useable device. The electronic module 2 may have stored software allowing it to interface with any computational device such as a computer, e.g. a PC or laptop, without losing functionality.

The re-useable electronic module 2 also allows the compatible drug delivery device 1 to be disposable; as a significant amount of complexity can be removed from the drug delivery device 1 with a limited number of metallic components.

The connector 7 of the electronic module 2 may be arranged as a universal or standard connector, for example in one of the formats USB, USB-B, Mini USB, Micro USB, IEEE1394, computer serial port (RS232), or a standard or proprietary connector of a flash memory card, such as SD Card, Mini SD Card, Micro SD Card, MultiMediaCard, CompactFlash, Memory Stick, and/or the like.

FIG. 1 is a schematic perspective view of an exemplary embodiment of the electronic module 2 and a corresponding drug delivery device 1. The electronic module 2 is adapted to be laterally arranged on the body 3 of the drug delivery device 1 and interface to the port 6 in a rear end of the drug delivery device 1 such that the drug delivery device 1 and the electronic module 2 form an ergonomic and functional unit when connected.

Figure 2:
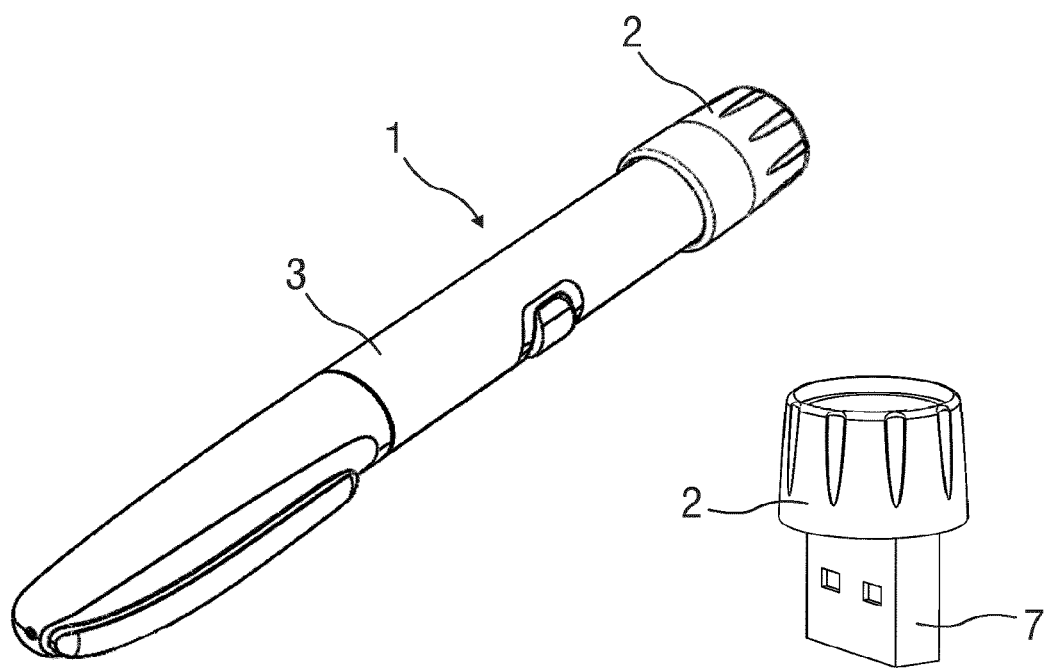
FIG. 2 is a schematic perspective view of another exemplary embodiment of the electronic module and a corresponding drug delivery device.

FIG. 2 is a schematic perspective view of another exemplary embodiment of the electronic module 2 and a corresponding drug delivery device 1. The electronic module 2 is shaped as a button and arranged to be assembled to a rear end of the drug delivery device 1 such that the drug delivery device 1 and the electronic module 2 form an ergonomic and functional unit when connected.

The electronic module 2 preferably comprises a connector 7, such as a USB connector, to have the ability to directly interface with any computer having a universal port. If the same connector 7 is used to connect to the drug delivery device 1 and/or a blood glucose meter the ports 6 of these devices should comply with the same standard as the connector 7, e.g. USB. This may result in attempts of the user to assemble generic devices of this standard, e.g. USB sticks, to the drug delivery device 1. This should be avoided in order to ensure users do not think data is being recorded when a generic device is connected and to avoid potential data corruption.

In order to address this problem the electronic module 2 and the drug delivery device 1 may be modified as illustrated in FIGS. 3 to 10.

Figure 3:
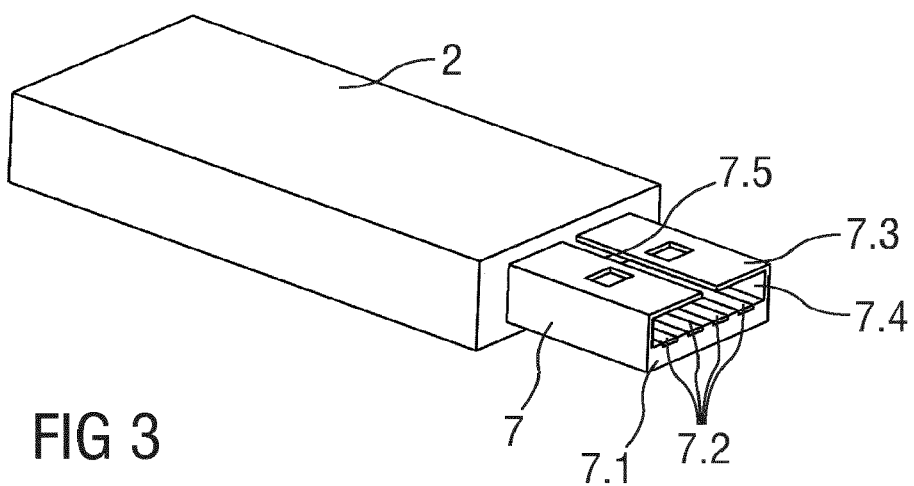
FIG. 3 is a schematic perspective view of an exemplary embodiment of the electronic module having a connector with a slot.
Figure 4:
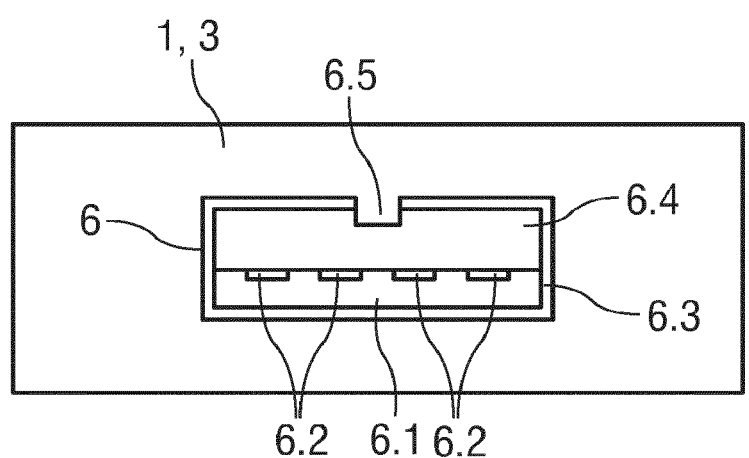
FIG. 4 is a schematic view of a drug delivery device with a port having a protrusion for engaging the slot of the connector of the electronic module of FIG. 3.

FIG. 3 is a schematic perspective view of an exemplary embodiment of the electronic module 2. FIG. 4 is a schematic view of a corresponding drug delivery device 1. The connector 7 substantially complies with a standard form such as USB. In this case the connector 7 comprises a contact carrier 7.1 retaining four electric contacts 7.2 arranged within a connector frame 7.3, which may be rectangular and comprise or consist of sheet metal. The electric contacts 7.2 are accessible through an opening in the connector frame 7.3. The contact carrier 7.1 and the electric contacts 7.2 fill only a portion of the space within the connector frame 7.3 while another portion 7.4 is empty.

The port 6 on the drug delivery device 1 likewise comprises a contact carrier 6.4 which corresponds to empty portion 7.4 of the connector 7. The contact carrier 6.4 retains four electric contacts 6.2 arranged within an empty connector frame 6.3 within body 3. The empty connector frame 6.3 corresponds to and is configured to receive connector frame 7.3 of the connector 7. Empty connector frame 7.3 may be rectangular and be shielded by sheet metal. The electric contacts 6.2 are accessible through an opening in the connector frame 6.3. The contact carrier 6.4 and the electric contacts 6.2 fill only a portion of the space within the connector frame 6.3 while another portion 6.1 is empty. The connector frame 6.3 of the port 6 is dimensioned to allow insertion of the connector frame 7.3 of the connector 7 wherein the contact carrier 7.1 of the connector 7 enters the empty portion 6.1 within the connector frame 6.3 of the port 6 while the contact carrier 6.4 of the port 6 enters the empty portion 7.4 within the connector frame 7.3 of the connector 7 such that each electric contact 6.2 of the port 6 contacts a respective electric contact 7.2 of the connector 7.

In order to ensure only the correct electronic module 2 is connected to the drug delivery device 1 at least one slot 7.5 is cut into the connector frame 7.3 of the connector 7 on the electronic module 2. The port 6 on the drug delivery device 1 and/or on the blood glucose meter comprises a protrusion 6.5 arranged to engage the slot 7.5. The protrusion 6.5 may be part of the body 3 protruding through a slot into the connector frame 7.3. The protrusion 6.5 in the port 6 blocks the fitting of a standard connector while the slot 7.5 in the modified connector 7 does not prevent fitting to standard ports 6.

In alternative embodiments the connector 7 of the electronic module 2 may have more than one slot 7.5 and the port 6 of the drug delivery device 1 may have a corresponding number of protrusions 6.5.

Figure 5:
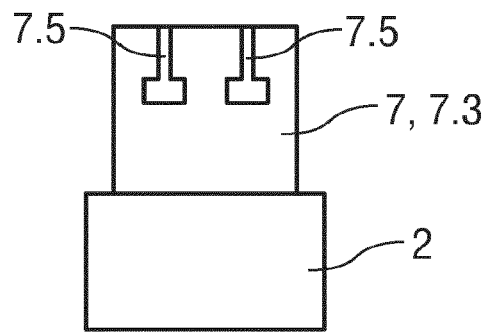
FIG. 5 is a detail side view of an exemplary embodiment of the electronic module having a connector with two slots.

FIG. 5 is a detail side view of an exemplary embodiment of the electronic module 2 having a connector 7 with two slots 7.5.

Figure 6:
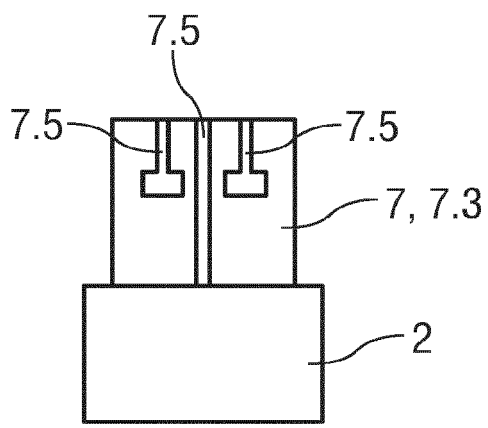
FIG. 6 is a detail side view of an exemplary embodiment of the electronic module having a connector with three slots.

FIG. 6 is a detail side view of an exemplary embodiment of the electronic module 2 having a connector 7 with three slots 7.5.

In alternative embodiments the connector 7 of the module 2 may comprise at least one different recess feature for interfacing with a corresponding protrusion on the port 6 of the drug delivery device 1.

Figure 7:
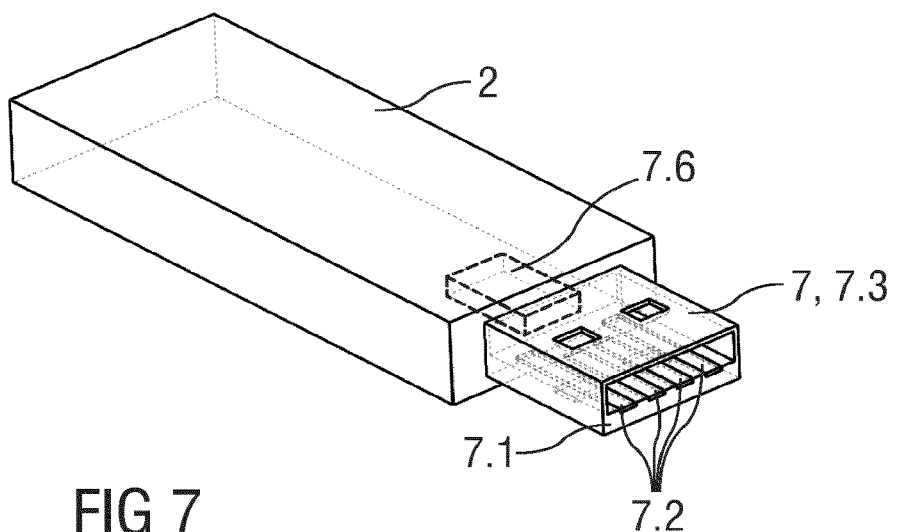
FIG. 7 is a perspective view of an exemplary embodiment of the electronic module, wherein a recess is arranged in the electronic module behind the connector.
Figure 8:
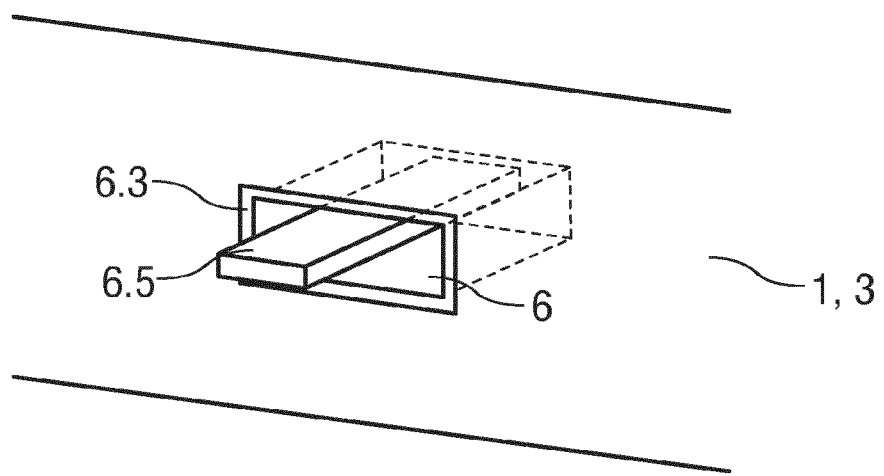
FIG. 8 is a perspective detail view of an exemplary embodiment of the drug delivery device with a port having a protrusion for engaging the recess of the connector of the electronic module of FIG. 7.

FIG. 7 is a perspective view of an exemplary embodiment of the electronic module 2, wherein a recess 7.6 is arranged in the electronic module 2 behind the connector 7. FIG. 8 is a perspective detail view of an exemplary embodiment of the drug delivery device 1, wherein a protrusion 6.5 passing through and extending from the connector frame 6.3 of the port 6 is arranged to engage in the recess 7.6 of the electronic module 2 in the electronic module 2 behind the connector 7. The protrusion 6.5 on the port 6 blocks the fitting of a standard connector while the recess 7.6 in the modified connector 7 does not prevent fitting to standard ports 6.

Figure 9:
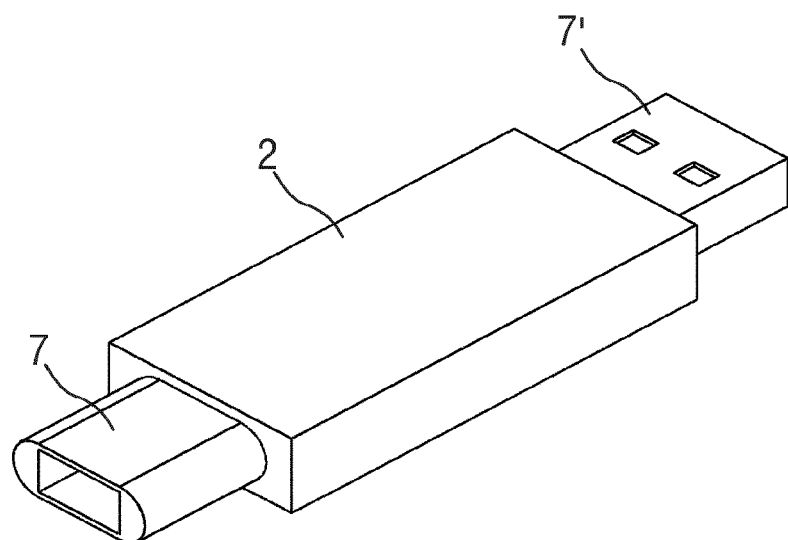
FIG. 9 is a perspective view of an exemplary embodiment of the electronic module having a bespoke or customized first connector and a universal second connector.
Figure 10:
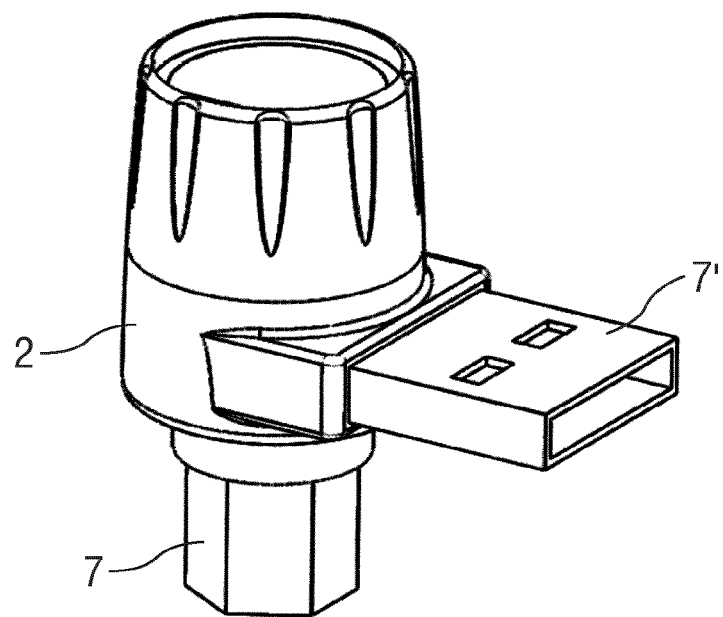
FIG. 10 is a perspective view of another exemplary embodiment of the electronic module having a bespoke or customized first connector and a universal second connector.

Another option for preventing the user from assembling generic devices to the drug delivery device 1 is illustrated in FIGS. 9 and 10.

FIG. 9 is a perspective view of an exemplary embodiment of the electronic module 2 having a bespoke or customized first connector 7 adapted to interface with a correspondingly shaped port in the drug delivery device (not illustrated) and a universal second connector 7' adapted to interface with universal ports in other equipment such as a computer. The electronic module 2 is suitable to be laterally arranged on the body 3 of a drug delivery device 1 similar to the one illustrated in FIG. 1 and interface with the first connector 7 to the port 6 in a rear end of the drug delivery device 1 such that the drug delivery device 1 and the electronic module 2 form an ergonomic and functional unit when connected. The connectors 7, 7' are arranged on opposed ends of the electronic module 2.

FIG. 10 is a perspective view of an exemplary embodiment of the electronic module 2 having a bespoke or customized first connector 7 adapted to interface with a correspondingly shaped port in the drug delivery device (not illustrated) and a universal second connector 7' adapted to interface with universal ports in other equipment such as a computer. The electronic module 2 is shaped as a button and suited to be assembled to a rear end of a drug delivery device 1 similar to the one illustrated in FIG. 2 such that the drug delivery device 1 and the electronic module 2 form an ergonomic and functional unit when connected. The first connector 7 is arranged on an end of the electronic module 2 arranged to connect to the drug delivery device 1 while the second connector 7' is aligned at right angles relative to the first connector 7.

A dose size delivered or to be delivered may be acquired and encoded so that it can be stored and processed by the electronic module 2. Acquisition and encoding of the dose size has to be performed within the drug delivery device 1, e.g. by means of mechanical contacts. In order to encode an 80 unit dose 7 bits and accordingly 7 contacts are needed as 80 is greater than $2^6=64$ but smaller than $2^7=128$. However, the connectors 7 of the electronic module 2 described above comply with the USB standard and therefore comprise four electric contacts 7.2 thus limiting the number of units that can be transferred from the drug delivery device 1 to the electronic module 2 without further circuitry in the drug delivery device 1 to $2^4=16$. Transferring a wider range of unit values over the port 6 may be achieved by serializing the acquired values by respective circuitry in the drug delivery device 1. However, it may be preferred to arrange the drug delivery device 1 as a disposable device wherein as much of the electronic circuitry as possible would be arranged in the reusable electronic module 2 to reduce the cost of the drug delivery device 1. In this situation the injection device would preferably have no or as little circuitry as possible and comprise conductive track and contact arms, which could be connected to the circuitry in the electronic module 2 via the port 6 and the connector 7. In this case transferring a wider range of values requires a greater number of electric contacts 6.2, 7.2.

For example in order to encode an 80 unit dose 7 bits and accordingly 7 contacts are needed as 80 is greater than $2^6=64$ and smaller than $2^7=128$.

In order to address this problem the connector 7 may be modified as illustrated in FIGS. 11 to 15.

Figure 11:
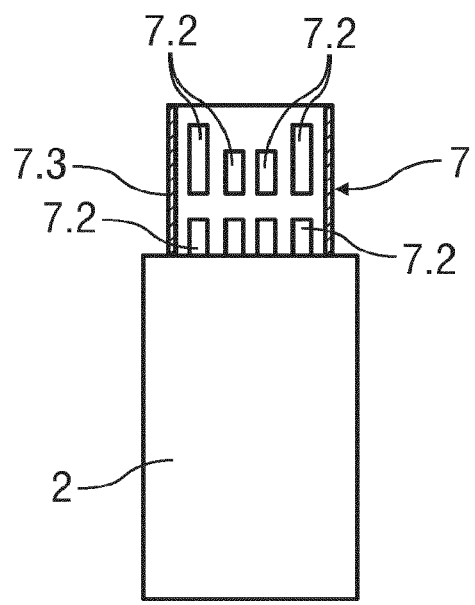
FIG. 11 is a schematic sectional view of an exemplary embodiment of the electronic module with a modified connector.

FIG. 11 is a schematic sectional view of an exemplary embodiment of the electronic module 2 with a modified connector 7. As opposed to the embodiments of FIGS. 3 and 7 which have four electric contacts 7.2 the contacts 7.2 in the embodiment of FIG. 11 are split transversally thus obtaining eight electric contacts 7.2. The port 6 of the drug delivery device 1 would also be modified to have eight corresponding electric contacts 6.2.

Figure 12:
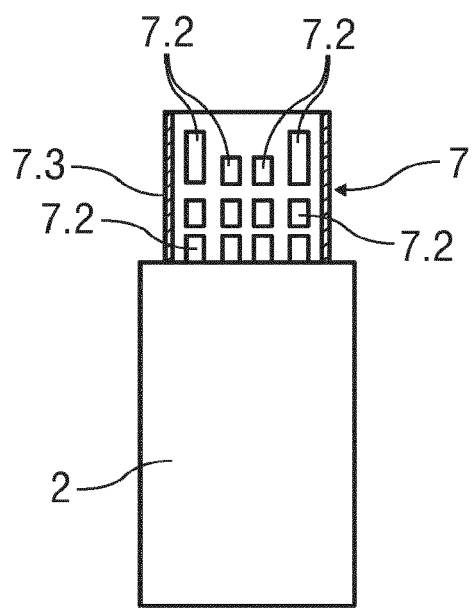
FIG. 12 is a schematic sectional view of another exemplary embodiment of the electronic module with a modified connector.

FIG. 12 is a schematic sectional view of an exemplary embodiment of the electronic module 2 with a modified connector 7. As opposed to the embodiments of FIGS. 3 and 7 which have four electric contacts 7.2 the contacts 7.2 in the embodiment of FIG. 12 are split twice transversally thus obtaining twelve electric contacts 7.2. The port 6 of the drug delivery device 1 would also be modified to have twelve corresponding electric contacts 6.2.

Figure 13:
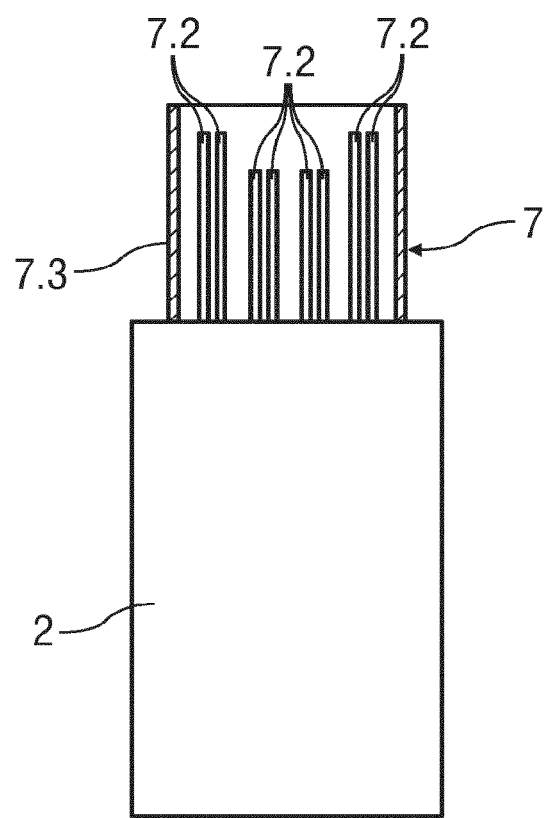
FIG. 13 is a schematic sectional view of yet another exemplary embodiment of the electronic module with a modified connector.

FIG. 13 is a schematic sectional view of an exemplary embodiment of the electronic module 2 with a modified connector 7. As opposed to the embodiments of FIGS. 3 and 7 which have four electric contacts 7.2 the contacts 7.2 in the embodiment of FIG. 13 are split longitudinally thus obtaining eight electric contacts 7.2. The port 6 of the drug delivery device 1 would also be modified to have eight corresponding electric contacts 6.2.

The electric contacts 7.2, 6.2 could be split more than twice thus obtaining 16 or another multiple of the number of electric contacts 7.2, 6.2 of the generic universal connector. This solution may be applied to other connectors 7 having a different generic number of electric contacts 7.2. The number of obtainable electric contacts 7.2 would then be a multiple of the generic number.

Figure 14:
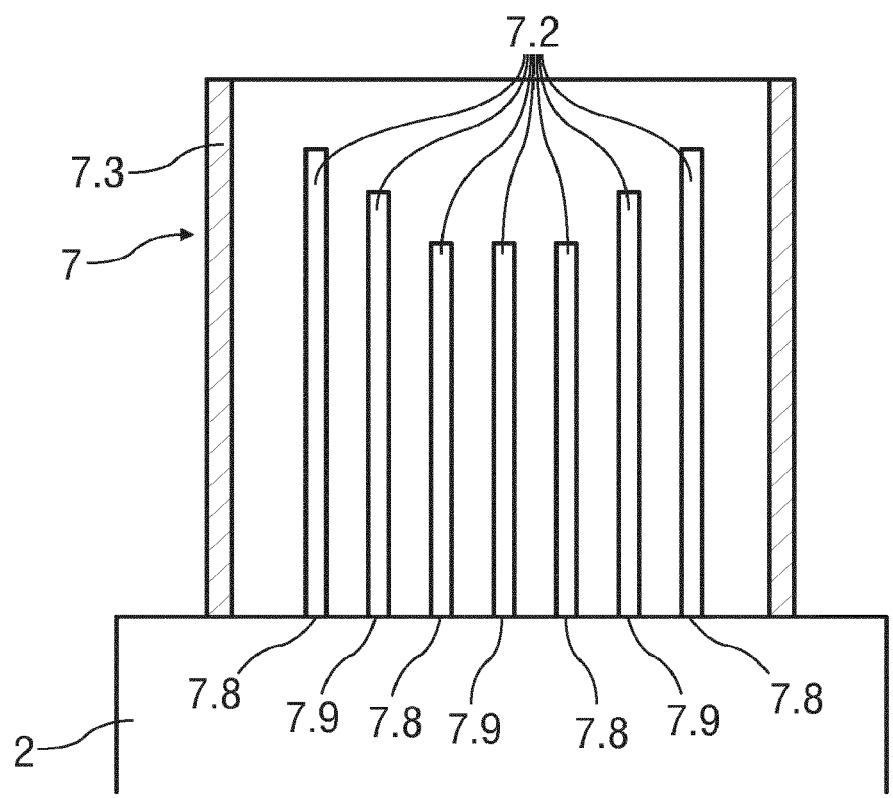
FIG. 14 is a schematic sectional view of yet another exemplary embodiment of the electronic module with a modified connector.

FIG. 14 is a schematic sectional view of an exemplary embodiment of the electronic module 2 with a modified connector 7. As opposed to the embodiments of FIGS. 3 and 7 which have four relatively wide electric contacts 7.2 in a first subset 7.8 of the generic electric contacts 7.2 in the embodiment of FIG. 14 the electric contacts 7.2 are narrowed and additional electric contacts 7.2 of a second subset 7.9 are arranged between the generic ones of the first subset 7.8 thus obtaining seven electric contacts 7.2. The port 6 of the drug delivery device 1 would also be modified to have seven corresponding electric contacts 6.2. In this solution, additional electric contacts 7.2 are placed in a region outside the standard four contact zones.

Figure 15:
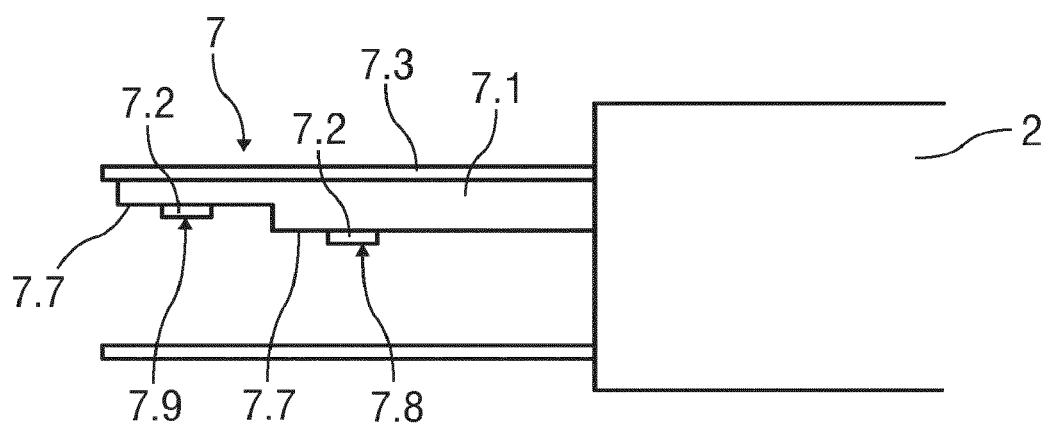
FIG. 15 is a schematic sectional view of yet another exemplary embodiment of the electronic module with a modified connector having a contact carrier with two different horizontal planes.

FIG. 15 is a schematic sectional view of an exemplary embodiment of the electronic module 2 with a modified connector 7. As opposed to the embodiments of FIGS. 3 and 7 which have four relatively wide electric contacts 7.2 arranged on the contact carrier 7.1 in one plane the modified connector 7 in FIG. 15 comprises a contact carrier 7.1 with two different horizontal planes 7.7 on which four electric contacts 7.2 of a first subset 7.8 and a second subset 7.9, are arranged, respectively thus obtaining eight electric contacts 7.2. The port 6 of the drug delivery device 1 would also be modified to have a contact carrier 6.4 with two different planes and eight electric contacts 6.2 corresponding to the electric contacts 7.2 of the modified connector 7. The modified contact carrier 6.4 of the port 6 would thus also block fitting of a generic connector to the drug delivery device 1.

The connectors 7 modified according to one of the FIGS. 11 to 15 would still allow to connect to a standard (USB) port of a computer.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence

H-His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O) 14, Asp28] Exendin-4(1-39)-Lys6-NH2,
des Met(O)14 Asp28 Pro36, Pro37, Pro38 Exendin-4(1-39)-NH2.
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-H2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A system comprising:
a drug delivery device comprising a customized port; and
an electronic device for recording information of the drug delivery device, the electronic device comprising a customized connector and a universal connector, the universal connector being selected from a group of universal connectors consisting of: USB, USB-B, Mini USB, Micro USB, IEEE1394, computer serial port (RS232), and a connector of a flash memory card,
wherein the universal connector is adapted to be connected to a universal port of a computer device, and the customized connector is adapted to be connectable to the customized port of the drug delivery device and to the universal port of the computer device, and
wherein the customized port includes a protrusion that allows connection of the customized connector to the customized port and prevents connection of the universal connector to the customized port.

2. The system of claim 1, further comprising a contact carrier retaining electric contacts of the customized connector,
wherein an insertion of the contact carrier into the drug delivery device results in a contact between the electric contacts of the customized connector and one or more electric contacts of the drug delivery device.

3. The system of claim 2, wherein the contact carrier is surrounded by the customized connector.

4. The system of claim 2, wherein the contact carrier has a first region adapted to be connected to the computer device through the universal connector and a second region adapted to be inserted into the drug delivery device through the customized connector.

5. The system of claim 4, wherein the universal connector is located between the customized connector and an inner portion of the electronic device.

6. The system of claim 5, wherein a first thickness of the first region differs from a second thickness of the second region, wherein the first and the second thicknesses are measured in a direction normal to a plane of the contact carrier that retains the electric contacts of the customized connector.

7. The system of claim 2, wherein the electronic device is configured to be connected to the computer device through an insertion of the electric contacts of the universal connector into the universal port of the computer device.

8. The system of claim 1, wherein at least one electronic contact of the customized connector is smaller than any electric contact of the universal connector.

9. The system of claim 1, wherein at least one electric contact of the customized connector is narrower than any electric contact of the universal connector.

10. The system of claim 1, wherein a number of electronic contacts of the customized connector is greater than a number of electronic contacts of the universal connector.

11. The system of claim 1, wherein the electronic device determines, through electric contacts of the customized connector, a dose size of drug delivered or to be delivered by the drug delivery device, wherein a number of the electric contacts of the customized connector limits a maximum dose size that the electronic device can determine.

12. The system of claim 2, wherein the customized connector covers an empty space in addition to covering the contact carrier, the empty space being dimensioned to allow insertion of the one or more electric contacts of the drug delivery device into the customized connector.

13. The system of claim 1, wherein the customized connector is located at a first end of the electronic device, and the electronic device further comprises a recess arranged within the electronic device and behind the customized connector such that when the customized connector is connected to the delivery device, a protrusion of the delivery device passes through the customized connector to be positioned in the recess.

14. The system of claim 1, wherein the customized connector includes a plurality of slots adapted to be engaged with a plurality of protrusions arranged on the customized port of the drug delivery device.

15. The system of claim 1, wherein the customized connector is shaped differently from the universal connector such that the customized connector includes a slot adapted to be engaged with a protrusion arranged in the customized port of the drug delivery device, the protrusion being configured to allow connection to the customized connector and to block connection to the universal port.

16. The system of claim 1, wherein the customized connector includes a slot or a recess that engages with the protrusion of the customized port when the customized connector is connected to the customized, and the universal connector lacks a corresponding slot or recess to engage with the protrusion of the customized port.

17. A system comprising:
a drug delivery device comprising a customized port; and
an electronic device for recording information of the drug delivery device, the electronic device comprising a customized connector and a universal connector, the universal connector being selected from a group of universal connectors consisting of: USB, USB-B, Mini USB, Micro USB, IEEE1394, computer serial port (RS232), and a connector of a flash memory card,
wherein the universal connector is adapted to be connected to a universal port of a computer device, and the customized connector is adapted to be connectable to the customized port of the drug delivery device and to the universal port of the computer device,
wherein the customized connector has a first number of electric contacts different from a second number of electric contacts on the universal connector,
wherein the electric contacts on the customized connector are split in a transversal direction or in a longitudinal direction once or more, thus having the first number of electric contacts on the customized connector to be a multiple of the second number of the electric contacts on the universal connector,
wherein the customized port has respective electric contacts split transversally or longitudinally once or more and according to the splits of the electric contacts of the customized connector, and
wherein moving from the customized connector towards an inner portion of the electronic device behind the customized connector defines the longitudinal direction, and moving along a direction normal to the longitudinal direction defines the transversal direction.

* * * * *